(12) United States Patent
Podányi et al.

(10) Patent No.: US 9,815,862 B2
(45) Date of Patent: Nov. 14, 2017

(54) POLYMORPHS OF LNNT (71) Applicant: Glycom A/S, Hørsholm (DK)

(72) Inventors: Benjámin Podányi, Dunakeszi (HU);
Gyula Dekany, Sinnamon Park (AU)

(73) Assignee: GLYCOM A/S, Hørsholm (DK)

( * ) Notice: Subject to any disclaimer, the term of this patent is extended or adjusted under 35 U.S.C. 154(b) by 0 days.

(21) Appl. No.: 14/653,086

(22) PCT Filed: Dec. 18, 2013

(86) PCT No.: PCT/DK2013/050436
§ 371 (c)(1),
(2) Date: Jun. 17, 2015

(87) PCT Pub. No.: WO2014/094783
PCT Pub. Date: Jun. 26, 2014

(65) Prior Publication Data
US 2015/0329580 A1    Nov. 19, 2015

(30) Foreign Application Priority Data

Dec. 18, 2012 (DK) ................................ 2012 70789

(51) Int. Cl.
| | | |
|---|---|---|
| C07H 15/12 | (2006.01) | |
| A23L 33/10 | (2016.01) | |
| A61K 31/702 | (2006.01) | |
| C07H 13/04 | (2006.01) | |
| A23L 33/00 | (2016.01) | |

(52) U.S. Cl.
CPC .............. C07H 15/12 (2013.01); A23L 33/10 (2016.08); A23L 33/40 (2016.08); C07H 13/04 (2013.01); *A23V 2002/00* (2013.01)

(58) Field of Classification Search
CPC .......... C07H 15/12; A23L 33/40; A23L 33/10
See application file for complete search history.

(56) References Cited

FOREIGN PATENT DOCUMENTS

| EP | 1405856 | 4/2004 |
|---|---|---|
| WO | WO2011100980 | 8/2011 |
| WO | WO2013091660 | 6/2013 |

OTHER PUBLICATIONS

Kuhn, R. et al, "Die konstitution der Lacto-N-neotetraose", Chem. Ber., including abstract, vol. 95, pp. 518-522, (1962).
Kuhn, R. et al, "Uber drei saure Pentasaccharide aus Frauenmilch" Chem. Ber., including abstract, vol. 95, p. 513, (1962).

*Primary Examiner* — Jonathan S Lau
(74) *Attorney, Agent, or Firm* — Neal, Gerber & Eisenberg LLP (57) ABSTRACT

A crystalline LNnT polymorph IV, characterized in that it displays X-ray powder diffraction reflections, based on a measurement using CuKα radiation, at 8.16, 15.41, 39.14, 23.77, 7.77 and 31.15 2Θ angles, and a crystalline LNnT polymorph V, characterized in that it displays X-ray powder diffraction reflections, based on a measurement using CuKα radiation, at 9.15, 10.26, 19.68, 26.06, 20.61 and 11.89 2Θ angles, are provided.

19 Claims, 6 Drawing Sheets

POLYMORPHS OF LNNT

CROSS REFERENCE TO RELATED APPLICATIONS

This is a national stage filing in accordance with 35 U.S.C. §371 of PCT/DK2013/050436, filed Dec. 18, 2013, which claims the benefit of the priority of Denmark Patent Application No. PA 2012 70789, filed Dec. 18, 2012, the contents of each are incorporated herein by reference.

FIELD OF THE INVENTION

The present invention provides two novel crystalline polymorphs of the tetrasaccharide LNnT, a method of making them and formulations containing the same.

BACKGROUND OF THE INVENTION

The human milk oligosaccharide lacto-N-neotetraose (LNnT) has previously been crystallized. Kuhn et al. [*Chem. Ber.* 1962, 95, 513, 518] originally isolated LNnT from a natural source and crystallized it (referred to as "LNnT polymorph I"). EP-A-1405856 disclosed that crystals of LNnT were obtained from aqueous acetone and proved by X-ray powder diffraction data (referred to as "LNnT polymorph II"). WO 2011/100980 disclosed another polymorph of LNnT having different melting point from that of Kuhn's crystals and a different X-ray powder diffraction pattern from that reported in EP-A-1405856 (referred to as "LNnT polymorph III").

Crystallization or recrystallization is one of the simplest and cheapest methods to separate a product from contaminants and obtain a pure substance. In addition, providing one or more crystalline modifications (polymorphs) of a solid compound is an important factor in product development, because the different crystalline forms affect the compound's properties—for example, thermodynamic stability, solubility, density, hygroscopicity, electrical properties (such as dielectric constant, conductivity), mechanical properties (such as friability, hardness, breaking strength, elasticity), optical properties (such as colour, transparency, refraction), etc.—diversely. Polymorphs enlarge the repertoire of materials that a scientist has available for improving the product's characteristics.

For this reason, ways have been sought for obtaining other polymorphs of LNnT which may be easier or less expensive to produce in crystalline form.

SUMMARY OF THE INVENTION

The present invention provides two novel crystalline polymorphs of LNnT, particularly novel crystalline LNnT polymorph IV and novel crystalline LNnT polymorph V. The present invention also provides methods for making the two novel crystalline polymorphs of LNnT that are believed suitable for their large scale production. Thus, the crystalline products of this invention are each a high purity LNnT that is suitable for nutritional and pharmaceutical products.

BRIEF DESCRIPTION OF THE FIGURES

The invention will be described in further detail hereinafter with reference to the accompanying figures, in which.

DETAILED DESCRIPTION OF THE :INVENTION

This invention provides the new LNnT crystalline polymorph IV. This crystalline LNnT polymorph IV comprises X-ray powder diffraction reflections, based on a measurement using CuKα radiation, at 8.16 2Θ angle, preferably at 8.16 and 15.41 2Θ angles, more preferably at 8.16, 15.41 and 39.14 2Θ angles, even more preferably at 8.16, 15.41, 39.14 and 23.77 2Θ angles, most preferably 8.16, 15.41, 39.14, 23.77 and 7.77 2Θ angles, in particular 8.16, 15.41, 39.14, 23.77, 7.77 and 31.15 2Θ angles. List of peaks of the MUD pattern of the crystalline LNnT polymorph IV is reported in Table 1.

TABLE 1

| 2Θ | rel. intensity |
|---|---|
| 7.77 | 40 |
| 8.16 | 100 |
| 9.36 | 4 |
| 11.08 | 1 |
| 13.08 | 1 |
| 15.41 | 48 |
| 15.64 | 9 |
| 16.29 | 15 |
| 18.71 | 3 |
| 19.36 | 1 |
| 19.76 | 1 |
| 23.16 | 6 |
| 23.77 | 46 |
| 24.52 | 5 |
| 25.52 | 2 |
| 26.76 | 3 |
| 31.15 | 34 |
| 31.50 | 8 |
| 32.87 | 4 |
| 33.88 | 2 |
| 35.04 | 5 |
| 39.14 | 47 |
| 39.91 | 3 |
| 40.60 | 2 |
| 41.40 | 1 |
| 47.31 | 18 |
| 48.58 | 2 |

This invention also provides the new LNnT crystalline polymorph V. This crystalline LNnT polymorph V comprises X-ray powder diffraction reflections, based on a measurement using CuKα radiation, at 9.15 2Θ angle, preferably at 9.15 and 10.26 2Θ angles, more preferably at 9.15, 10.26 and 19.68 2Θ angles, even more preferably at 9.15, 10.26, 19.68 and 26.06 2Θ angles, most preferably at 9.15, 10.26, 19.68, 26.06 and 20.61 2Θ angles, in particular 9.15, 10.26, 19.68, 26.06, 20.61 and 11.89 2Θ angles. List of peaks of the XRPD pattern of crystalline LNnT polymorph V is reported in Table 2.

TABLE 2

| 2Θ | rel. intensity |
|---|---|
| 5.56 | 3 |
| 9.15 | 100 |
| 10.26 | 78 |
| 11.89 | 50 |
| 13.72 | 4 |
| 16.12 | 7 |
| 17.50 | 38 |
| 18.08 | 7 |
| 19.14 | 36 |
| 19.68 | 71 |
| 20.61 | 63 |
| 21.01 | 35 |
| 21.84 | 16 |
| 23.40 | 13 |
| 24.72 | 11 |
| 25.48 | 13 |
| 26.06 | 68 |
| 26.48 | 30 |
| 28.27 | 8 |
| 29.36 | 10 |
| 30.80 | 8 |
| 32.37 | 16 |
| 34.04 | 9 |

The novel crystalline forms IV and V of LNnT, respectively, can be considered as an anomeric mixture of α- and β-anomers or even a pure form of one of the anomers.

The powder X-ray diffraction patterns of crystalline LNnT disclosed in EP-A-1405856 and WO 2011/100980 differ significantly from that of the crystals of the LNnT polymorphs and V of this invention. Moreover, the powder X-ray diffraction patterns of crystalline LNnT polymorphs IV and V of this invention are also different from each other. The notable differences show that the crystalline LNnT polymorphs IV and V of this invention are novel and different polymorphs.

Preferably, each of the crystalline LNnT polymorphs IV and V of this invention is substantially pure. The expression "substantially pure" preferably means that the crystalline LNnT polymorph contains less than 10 w/w % of impurity, preferably less than 5 w/w % of impurity, more preferably less than 1 w/w % of impurity, most preferably less than 0.5 w/w % of impurity, in particular less than 0.1 w/w % of impurity, wherein "impurity" refers to any physical entity different from the novel crystalline LNnT polymorph, such as an amorphous LNnT, different LNnT polymorph(s), unreacted intermediate(s) remained from the synthesis of LNnT, by-product(s), degradation product(s), inorganic salt(s) and/or other contaminants different from organic solvent(s) and/or water.

Also preferably, each of the crystalline LNnT polymorphs IV and V of the invention is substantially free from any organic solvents. The expression "substantially free from any organic solvents" preferably means that the content of organic solvent(s) is at most 1000 ppm, preferably at most 800 ppm, more preferably at most 600 ppm, most preferably at most 400 ppm and in particular at most 200 ppm.

This invention further provides a method for preparing the crystalline LNnT polymorph IV in the following way: amorphous or crystalline, preferably amorphous, LNnT is dissolved in water to obtain a thick solution of at least 25 w/w %, preferably at least 30 w/w %, particularly about 34-36 w/w %, then stored at 2-25° C. for 1-4 weeks, but preferably at 2-5° C. for 1 week, during which time the polymorph precipitates. The crystalline LNnT polymorph IV, after drying at 40-60 ° C. and atmospheric pressure contains 11.3 m/m % of water which corresponds 5 molecules of crystalline water.

This invention still further provides a method for preparing the crystalline LNnT polymorph V in the following way: crystalline LNnT polymorph IV is dried in vacuum (under 75 mBar, preferably between 10-50 mBar) at 40-60° C. until its weight remains unchanged (generally 2-3 hours), Its recorded XRPD diagram shows a significantly different pattern from that of polymorph IV. If the so-formed crystalline LNnT polymorph V is stored in an open vessel at ambient temperature and humidity for a week, no substantial change in its XRPD pattern can be observed.

Generally, LNnT polymorphs have previously been obtained by antisolvent crystallization (water/ethanol: Kuhn et al. [Chem. Ber. 1962, 95, 513, 518]; water/acetone: EP-A-1405856; water/methanol: WO 2011/100980). Scale-up of this type of crystallization has required careful mixing of the antisolvent, both at the point of addition and in circulation of the bulk. Insufficient control of local mixing at the point of addition risked local supersaturation and excessive nucleation. Moreover, the used solvent mixture required separation for recovery for recycling and/or to satisfy environmental regulations. In addition, the antisolvent (generally an organic solvent) always remained in small amounts adsorbed on the surface of the crystal particles, even after extensive drying, which risked limiting the particles' usefulness as a component in a pharmaceutical or nutritional formulation subject to strict regulatory requirements. These problems can be overcome straightforwardly by crystallizing LNnT from just water, thus avoiding the use of an organic solvent.

Each of the crystalline polymorphs IV and V of LNnT according to this invention is suitable for pharmaceutical and nutritional use. In this regard, LNnT, alone or in combination with other N-acetyllactosamine and/or fucose and/or sialic acid containing human milk oligosaccharides, is particularly effective in the education and/or maturation of the immune system of neonatal infants, and have preventive effect against secondary infections following viral infections such as influenza. The use of LNnT as prebiotic enhances the beneficial effects and efficiency of probiotics, such as *Lactobacillus* and *Bifidobacterium* species, in promoting the development of an early bifidogenic intestinal microbiota in infants, in reducing the risk of development or allergy and/or asthma in infants, in preventing and treating pathogenic infections in such as diarrhoea in infants.

Also in accordance with this invention, a pharmaceutical composition is provided comprising the crystalline polymorph IV or V of LNnT of the invention, or their combination, as an active ingredient and one or more pharmaceutically acceptable carriers such as additives, adjuvants, excipients and diluents (water, gelatine, talc, sugars, starch, gum arabic, vegetable gums, vegetable oils, polyalkylene glycols, flavouring agents, preservatives, stabilizers, emulsifying agents, lubricants, colorants, fillers, wetting agents, etc.). Suitable carriers are described in the most recent edition of Remington's Pharmaceutical Sciences, a standard reference text in the field. The dosage form for administration includes, for example, tablets, powders, granules, pills, suspensions, emulsions, infusions, capsules, syrups, injections, liquids, elixirs, extracts and tincture.

Also in accordance with this invention, the crystalline polymorph IV or V of LNnT of the invention, or their combination, can be used for the preparation of pharmaceutical compositions. Pharmaceutical compositions can be manufactured in a conventional manner, e.g., as described in the most recent edition of Remington's Pharmaceutical Sciences, a standard reference text in the field.

Further in accordance with this invention, a nutritional formulation (such as food, drink or feed) is provided comprising the crystalline LNnT polymorph IV or V of this invention, or their combination. The nutritional formulation can also contain edible micronutrients, vitamins and minerals as well. The amounts of such ingredient can vary depending on whether the formulation is intended for use with normal, healthy infants, children, adults or subjects having specialized needs (e.g. suffering from metabolic disorders), Micronutrients include for example edible oils, fats or fatty acids (such as coconut oil, soy-bean oil, monoglycerides, diglycerides, palm olein, sunflower oil, fish oil, linoleic acid, linolenic acid etc.), carbohydrates (such as glucose, fructose, sucrose, maltodextrin, starch, hydrolysed cornstarch, etc.) and proteins from casein, soy-bean, whey or skim milk, or hydrolysates of these proteins, but protein from other source (either intact or hydrolysed) may be used as well. Vitamins may be chosen from the group consisting of vitamin A, B1, B2, B5, B6, B12, C, D, E, H, K, folic acid, inositol and nicotinic acid. The nutritional formulation can also contain the following minerals and trace elements: Ca, P, K, Na, Cl, Mg, Mn, Fe, Cu, Zn, Se, Cr or I.

In a preferred embodiment, the nutritional formulation is an infant formula, i.e. a foodstuff intended for use by infants during the first 4-6 months of life and satisfying, by itself, the nutritional requirements of infants. It can contain one or more probiotic *Bifidobacterium* species, prebiotics such as fructooligosaccharides and galactooligosaccharides, proteins from casein, soy-bean, whey or skim milk, carbohydrates such as lactose, saccharose, maltodextrin, starch or mixtures thereof, lipids (e.g. palm olein, sunflower oil, safflower oil) and vitamins and minerals essential in a daily diet. The infant formula preferably contains the crystalline LNnT polymorph IV or V of the invention, or their combination, in a total amount of 0.1-3.0 g/100 g of formula.

In another preferred embodiment, the nutritional formulation can be a food supplement containing the crystalline LNnT polymorph IV or V of the invention, or their combination. The food supplement can also contain one or more probiotics in an amount sufficient to achieve the desired effect in an individual, preferably in children and adults. The food supplement can also contain vitamins, minerals, trace elements and other micronutrients as well. The food supplement may be for example in the form of tablets, capsules, pastilles or a liquid. The supplement can also contain conventional additives, such as binders, coatings, emulsifiers, solubilising agents, encapsulating agents, film forming agents, adsorbents, carriers, fillers, dispersing agents, wetting agents, jellifying agents, gel forming agents, etc. The daily dose of LNnT typically ranges from 0.1 to 3.0 g.

According to a more preferred embodiment, the food supplement is a digestive health functional food as the administration of LNnT provides a beneficial effect on digestive health. Digestive health functional food is a processed food used with intention enhance and preserve digestive health by crystalline LNnT according to the present invention as physiologically functional ingredient or component in forms of tablet, capsule, powder, etc. Different terms such as dietary supplement, nutraceutical, designed food, health product may also be used to refer to functional food.

In a further embodiment, the crystalline LNnT polymorph IV or V of the invention, or their combination, is used for the preparation of nutritional formulations, such as foods, drinks and feeds, preferably infant formulas, food supplements and digestive health functional food. The nutritional formulations can be prepared in a conventional manner. For example, it can be prepared by admixing micronutrient components in appropriate proportions, and then adding vitamins and minerals while avoiding thermal degradation or decomposition of heat sensitive vitamins by adding them after homogenization. Lipophilic vitamins can be dissolved in a fat source before mixing. A liquid mixture is formed using water, whose temperature is preferably about 50-80° C. to help dissolution or dispersal of the ingredients. The crystalline LNnT polymorph IV or V, or their combination, can be suitably added at this stage. The resulting mixture is then homogenized by flash heating to about 80-150° C. by means of steam injection, heat exchanger or autoclave. This thermal treatment also reduces significantly the bacterial load. The hot mixture is then cooled rapidly to about 60-80° C. If needed, further homogenization can be carried out at this temperature under high pressure of about 2-30 MPa. After cooling, heat sensitive constituents can be added, and the pH and the solids content can be conveniently adjusted. The resulting mixture is then dried in a conventional manner, such as by spray drying or freeze drying to powder, Probiotics can be added at this point by dry-mixing.

Other features of the invention will become apparent in the course of the following descriptions of exemplary embodiments which are given for illustration of the invention and are not to be limiting thereof.

EXAMPLES

Example 1

LNnT Polymorph IV

Amorphous spray-dried LNnT (6.0087 g, water content: 2.67%, purity: 99.2% by HPAEC) was dissolved in HPLC water (10.66 ml). Dissolution was reached by shaking. Two samples of 1 ml solution were stored at 2-8° C. (sample 1) and room temperature (sample 2), respectively, for 4 weeks. A white precipitation appeared at the end of the first week, which can be redissolved only when ultrasonicated for 3 hours at 50° C. The precipitation was collected by filtration and dried at atmospheric pressure.

Figure 1:
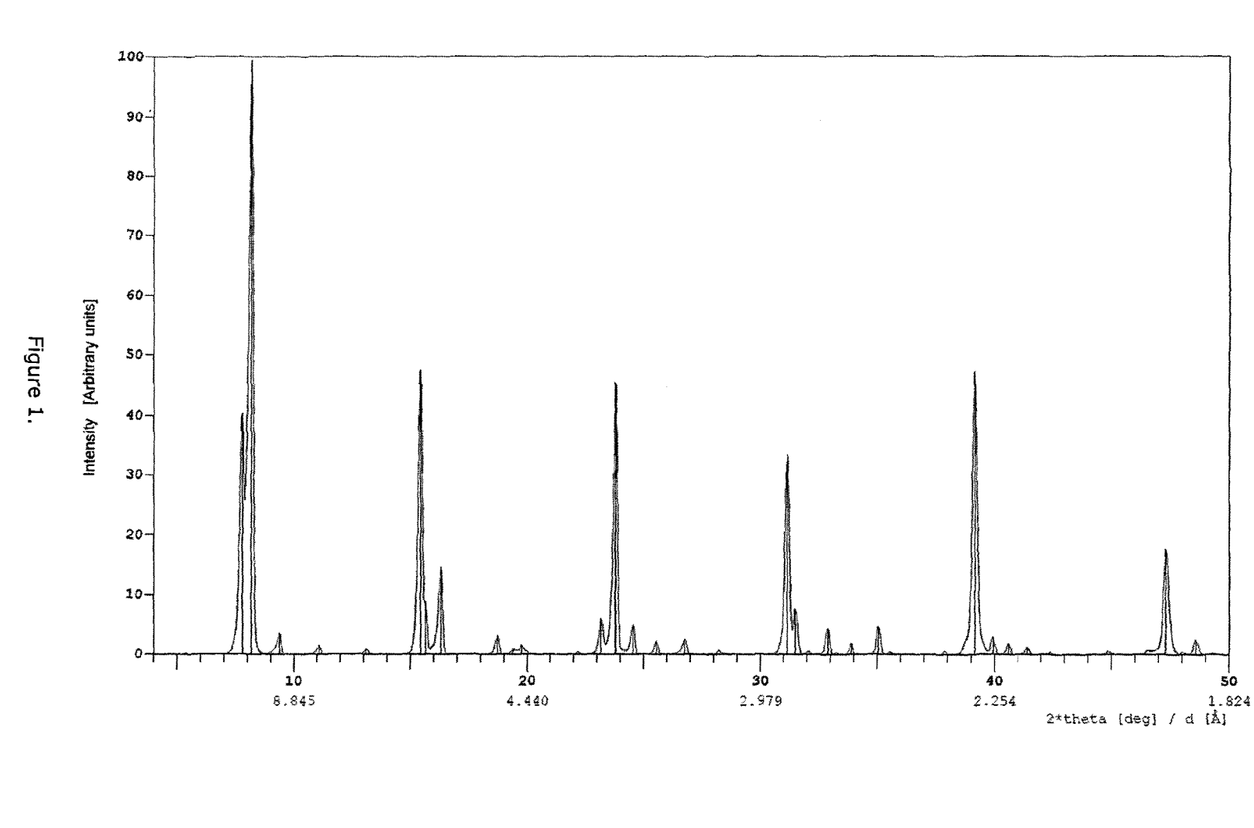
FIG. 1 shows the X-ray powder diffraction pattern of the novel crystalline LNnT polymorph IV of this invention.

XRPD investigation of the collected crystals was conducted with a Philips PW 1830/PW 1050 instrument in transmission geometry, using CuK$\alpha$ radiation made monochromatic by means of a graphite monochromator. D-spacings were calculated from the 2$\Theta$ values, based on a wavelength of 1.54186 Å. As a general rule the 2$\Theta$ values have an error rate of ±0.2 Å. The recorded XRPD diagram is shown in FIG. 1.

Example 2

LNnT Polymorph IV

Amorphous spray-dried LNnT (12.0 g) was dissolved in 23.0 ml of HPLC water. The solution was put into refrigerator (2-5° C.). After one week the solution became a crystalline block. The filtered crystals were dried at 50° C.

for 7 hours at an oven and thereafter at room temperature at ambient humidity. This material was investigated by XRPD (see above). Its diagram was identical with that of the sample according to example 1.

Example 3

LNnT Polymorph V

Figure 2:
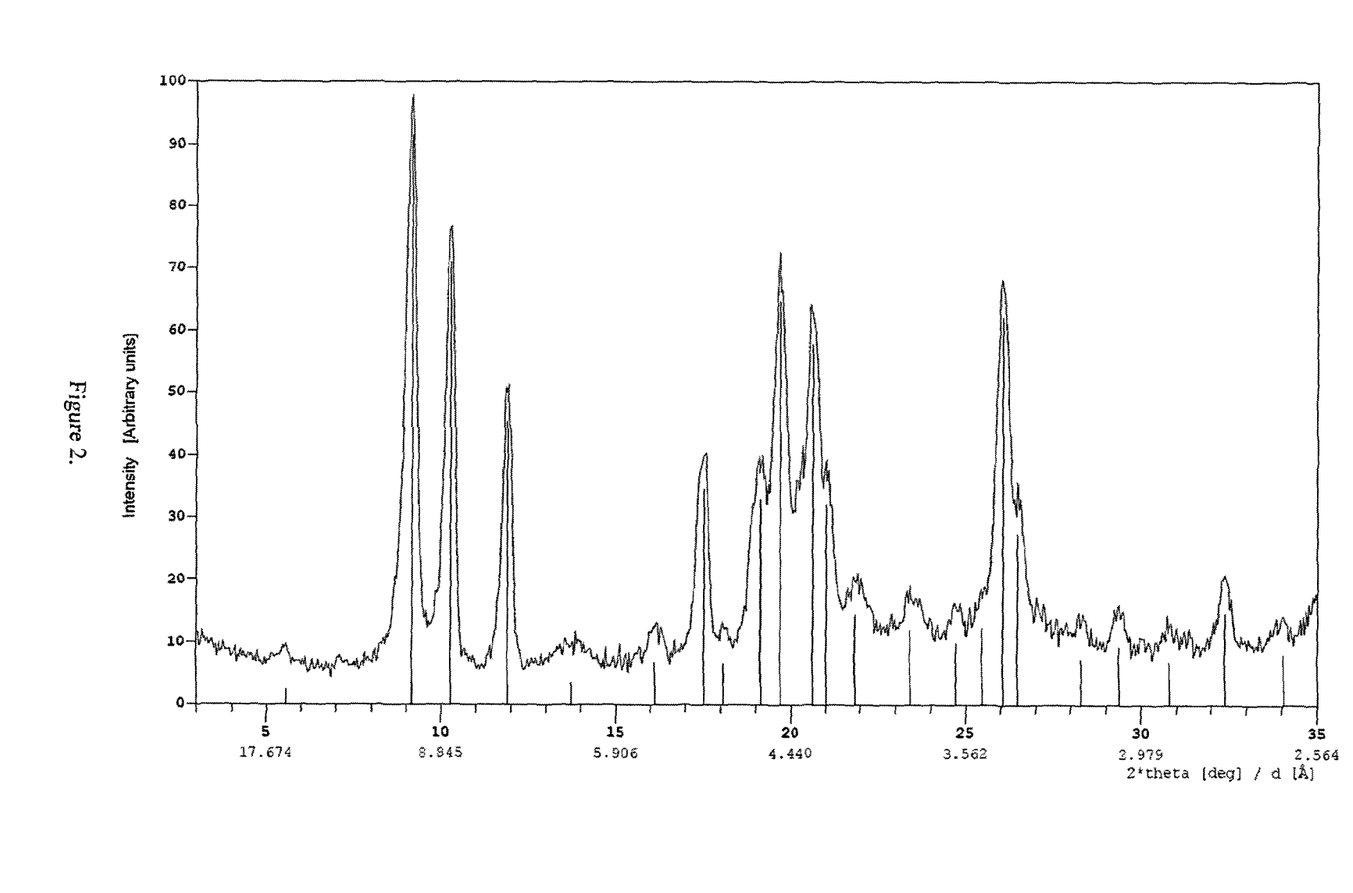
FIG. 2 shows the X-ray powder diffraction pattern of the novel crystalline LNnT polymorph V of this invention.
Figure 3:
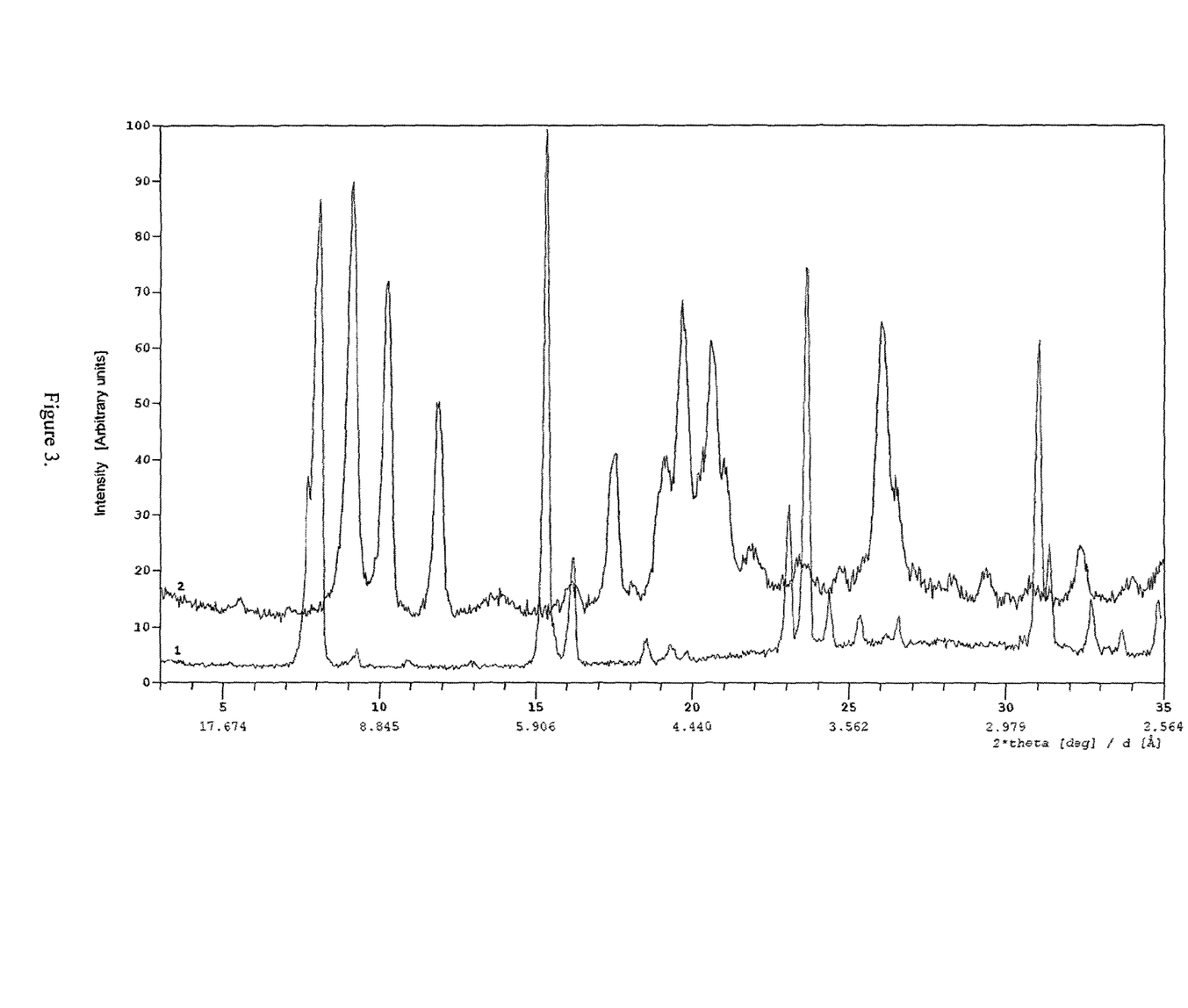
FIG. 3 shows the X-ray powder diffraction pattern of the novel crystalline LNnT polymorph IV (pattern 1) compared to that of the novel crystalline LNnT polymorph V (pattern 2)
Figure 4:
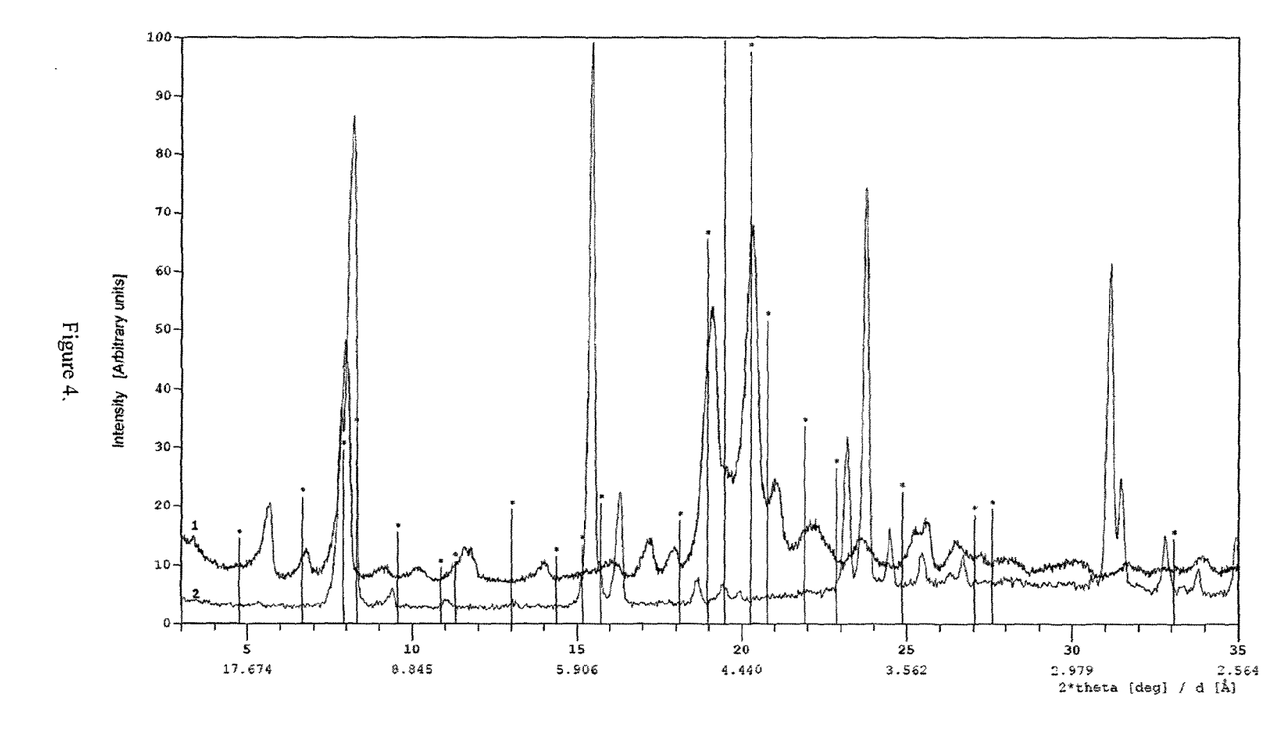
FIG. 4 shows the X-ray powder diffraction patterns of the crystalline LNnT polymorphs II (values with *) and III (pattern 1) compared to that of the novel crystalline LNnT polymorph IV (pattern 2)
Figure 5:
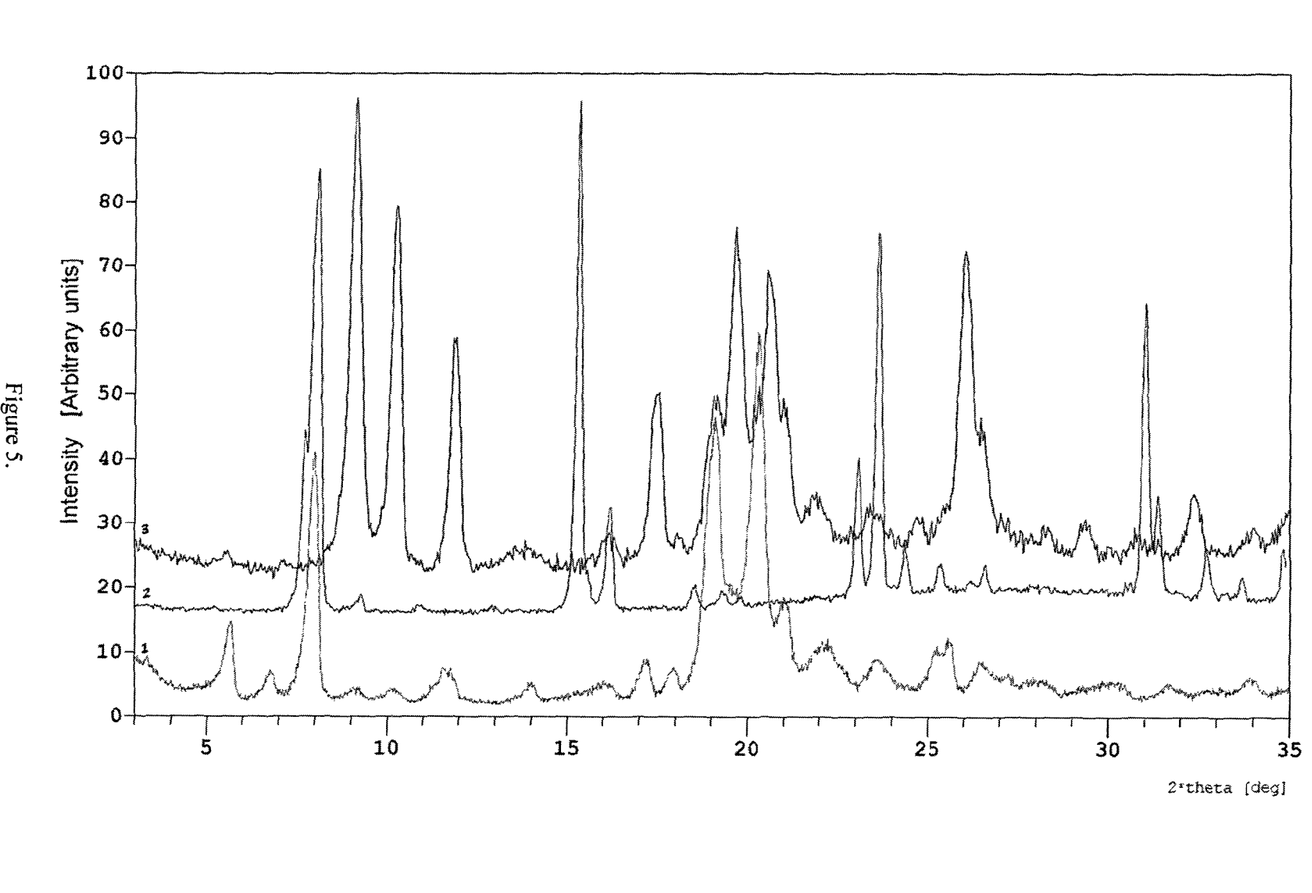
FIG. 5 shows the X-ray powder diffraction pattern of the crystalline LNnT polymorphs III (pattern 1) compared to those of the novel crystalline LNnT polymorph IV (pattern 2) and V (pattern 3)
Figure 6:
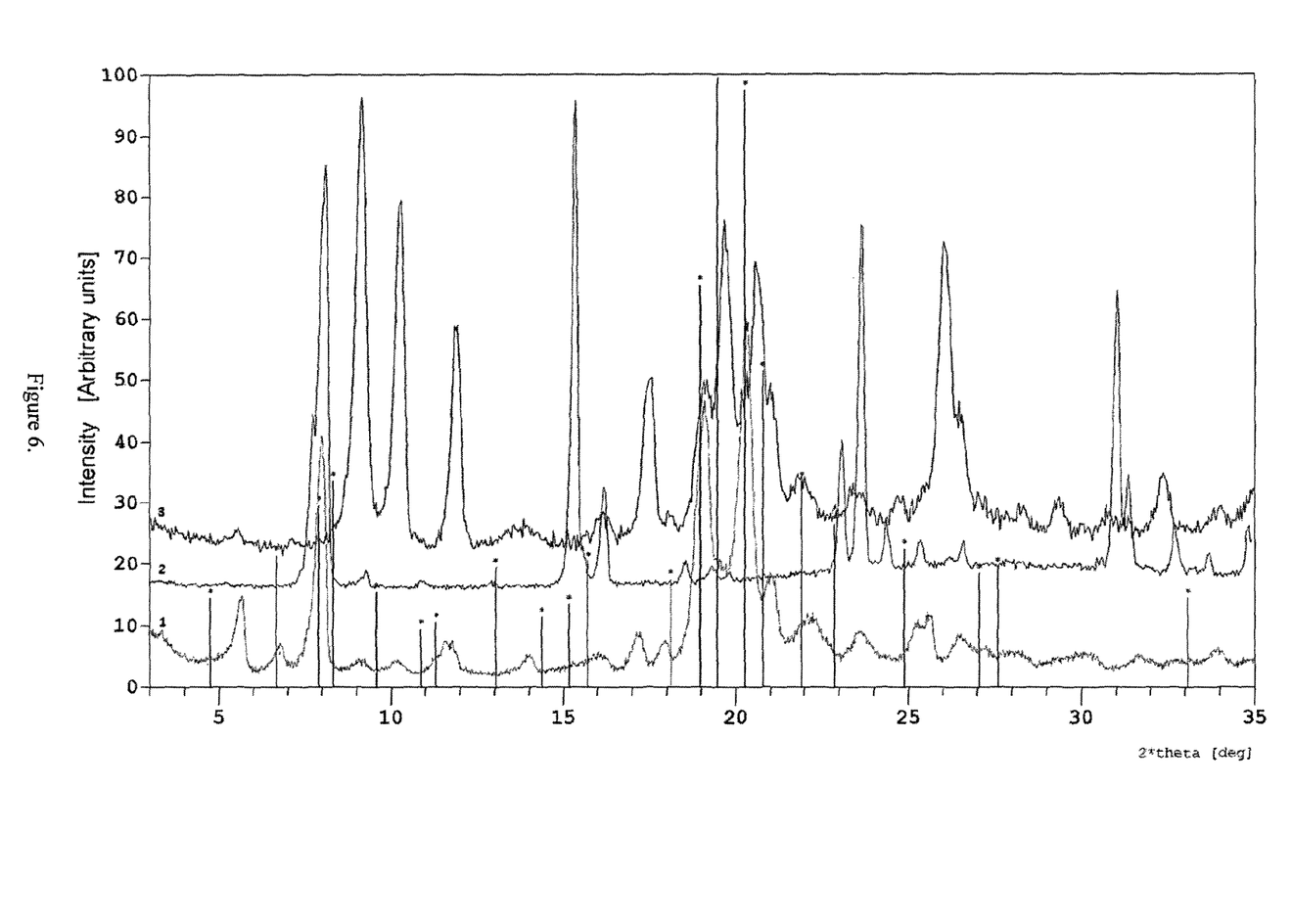
FIG. 6 shows the X-ray powder diffraction patterns of the crystalline LNnT polymorphs II (values with *) and III (pattern 1) compared to those of the novel crystalline LNnT polymorph IV (pattern 2) and V (pattern 3).

The LNnT polymorph IV according to example 2 (water content: 11.3% by Karl Fischer titration) was dried in vacuum oven at 50° C. The weight loss was measured to be 10.9% and 11.4% after 1.5 and 2.5 hours, respectively. The sample was investigated by XRPD (see above). The recorded XRPD diagram is shown in FIG. 2.

The invention claimed is:

1. A crystalline LNnT polymorph IV, wherein the crystalline LNnT polymorph IV displays X-ray powder diffraction reflections, based on a measurement using CuKα radiation, at 8.16 2Θ, 15.41 2Θ, 39.14 2Θ, 23.77 2Θ, and 7.77 2Θ.

2. The crystalline LNnT polymorph IV of claim 1, wherein the crystalline LNnT polymorph IV is substantially pure.

3. The crystalline LNnT polymorph IV of claim 1, wherein the crystalline LNnT polymorph IV is substantially free from organic solvent.

4. The crystalline LNnT polymorph IV of claim 1 for use as a pharmaceutical agent.

5. A pharmaceutical composition comprising the crystalline LNnT polymorph IV of claim 1 and one or more pharmaceutically acceptable carriers.

6. A nutritional formulation comprising the crystalline LNnT polymorph IV of claim 1.

7. The nutritional formulation of claim 6, wherein the nutritional formulation is an infant formula.

8. The nutritional formulation of claim 6, wherein the nutritional formulation is a food supplement.

9. The food supplement of claim 8, wherein the food supplement is a digestive health functional food.

10. The crystalline LNnT polymorph IV of claim 1, wherein the crystalline LNnT polymorph IV displays X-ray powder diffraction reflections, based on a measurement using CuKα radiation, at 8.16 2Θ, 15.41 2Θ, 39.14 2Θ, 23.77 2Θ, 7.77 2Θ, and 31.15 2Θ.

11. A crystalline LNnT polymorph V, wherein the crystalline LNnT polymorph V displays X-ray powder diffraction reflections, based on a measurement using CuKα radiation, at 9.15 2Θ, 10.26 2Θ, 19.68 2Θ, 26.06 2Θ, and 20.61 2Θ.

12. A method for producing the crystalline LNnT polymorph IV of claim 1, wherein an aqueous solution of greater than 25 w/w % LNnT is stored at 2-25° C.

13. The crystalline LNnT polymorph IV of claim 11, wherein the crystalline LNnT polymorph V displays X-ray powder diffraction reflections, based on a measurement using CuKα radiation, at 9.15 2Θ, 10.26 2Θ, 19.68 2Θ, 26.06 2Θ, 20.61 2Θ, and 11.89 2Θ.

14. The crystalline LNnT polymorph V of claim 11, wherein the crystalline LNnT polymorph V is substantially pure.

15. The crystalline LNnT polymorph V of claim 11, wherein the crystalline LNnT polymorph V is substantially free from organic solvent.

16. The crystalline LNnT polymorph V of claim 11 for use as a pharmaceutical agent.

17. A pharmaceutical composition comprising the crystalline LNnT polymorph V of claim 11 and one or more pharmaceutically acceptable carriers.

18. A nutritional formulation comprising the crystalline LNnT polymorph V of claim 11.

19. A method for producing the crystalline LNnT polymorph V of claim 11, wherein the crystalline LNnT polymorph IV of claim 1 is dried under vacuum at 40-60° C.

* * * * *